United States Patent
Liu et al.

(10) Patent No.: US 7,018,673 B2
(45) Date of Patent: Mar. 28, 2006

(54) OXYGEN SENSOR AND EMISSION CONTROL SYSTEM

(75) Inventors: Meilin Liu, Norcross, GA (US); William Lynn Rauch, Atlanta, GA (US); Zuoyan Peng, Guilderland, NY (US)

(73) Assignee: Georgia Tech Research Corporation, Atlanta, GA (US)

( * ) Notice: Subject to any disclaimer, the term of this patent is extended or adjusted under 35 U.S.C. 154(b) by 462 days.

(21) Appl. No.: 10/228,889

(22) Filed: Aug. 27, 2002

(65) Prior Publication Data

US 2003/0034246 A1 Feb. 20, 2003

Related U.S. Application Data

(63) Continuation-in-part of application No. 09/453,283, filed on Dec. 2, 1999, now Pat. No. 6,440,283.

(60) Provisional application No. 60/110,628, filed on Dec. 2, 1998.

(51) Int. Cl.
*G01N 27/41* (2006.01)
*C25D 13/02* (2006.01)

(52) U.S. Cl. .................... 427/126.3; 204/426

(58) Field of Classification Search ........ 204/421–429; 205/783.5–785; 73/23.31–23.32; 427/115, 427/453, 126.3
See application file for complete search history.

(56) References Cited

U.S. PATENT DOCUMENTS

| | | | |
|---|---|---|---|
| 3,645,875 A | 2/1972 | Record et al. | 204/429 |
| 3,935,089 A | 1/1976 | Togawa et al. | 204/429 |
| 4,172,247 A | 10/1979 | Ikeura | 338/34 |
| 4,177,112 A | 12/1979 | Suzuki et al. | 205/784 |
| 4,940,528 A * | 7/1990 | Oki et al. | 204/427 |
| 5,173,166 A * | 12/1992 | Tomantschger et al. | 204/412 |
| 5,403,462 A * | 4/1995 | Lev et al. | 204/403.15 |
| 5,494,700 A * | 2/1996 | Anderson et al. | 427/115 |
| 5,538,620 A * | 7/1996 | Nikolskaja | 205/782 |
| 5,695,624 A | 12/1997 | Garzon et al. | 204/425 |
| 5,700,361 A * | 12/1997 | Shiomitsu et al. | 204/491 |
| 5,910,239 A * | 6/1999 | Maier et al. | 205/781 |
| 5,954,930 A | 9/1999 | Nafe et al. | 204/421 |
| 6,074,540 A | 6/2000 | Kroll et al. | 204/424 |
| 6,251,473 B1 * | 6/2001 | Wang et al. | 427/126.3 |
| 6,656,336 B1 * | 12/2003 | Mukundan et al. | 204/424 |

* cited by examiner

*Primary Examiner*—Kaj K. Olsen
(74) *Attorney, Agent, or Firm*—Thomas, Kayden, Horstemeyer & Risley LLP

(57) ABSTRACT

An emission control system is disclosed for determining a concentration of oxygen in a flow of gas which has a sensor. The sensor has a diffusion barrier, an electrolyte material, and a counter-electrode. The counter-electrode is configured to support the diffusion barrier, and the electrolyte material is disposed between the diffusion barrier and the counter electrode. Also disclosed is a method of producing the sensor and emission control system.

21 Claims, 18 Drawing Sheets

Gas 222

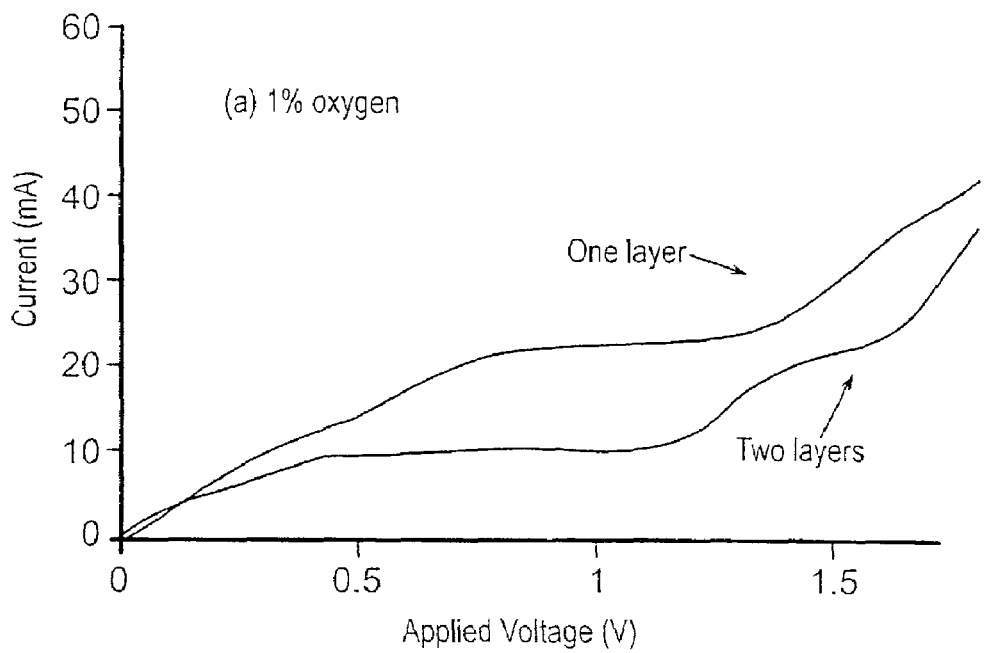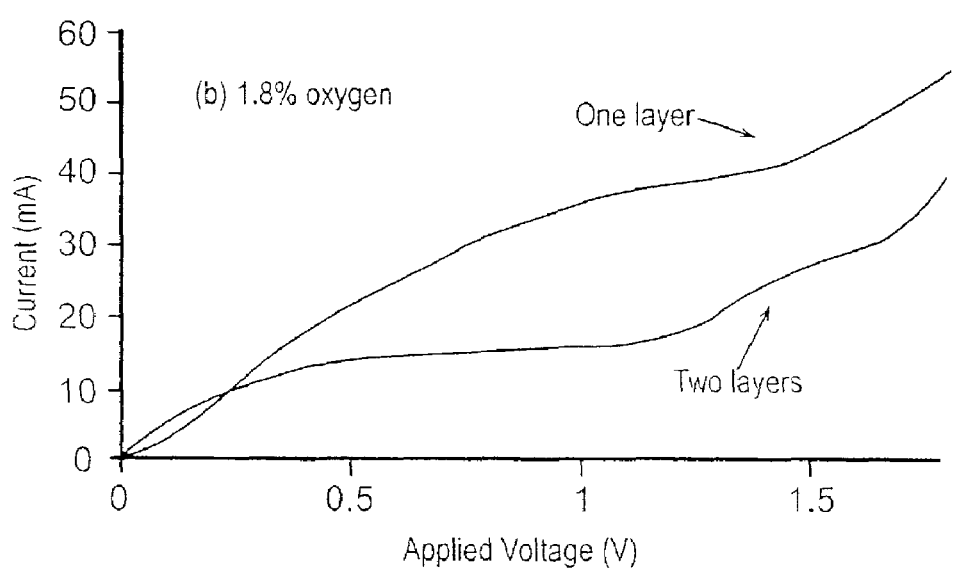
Fig. 6

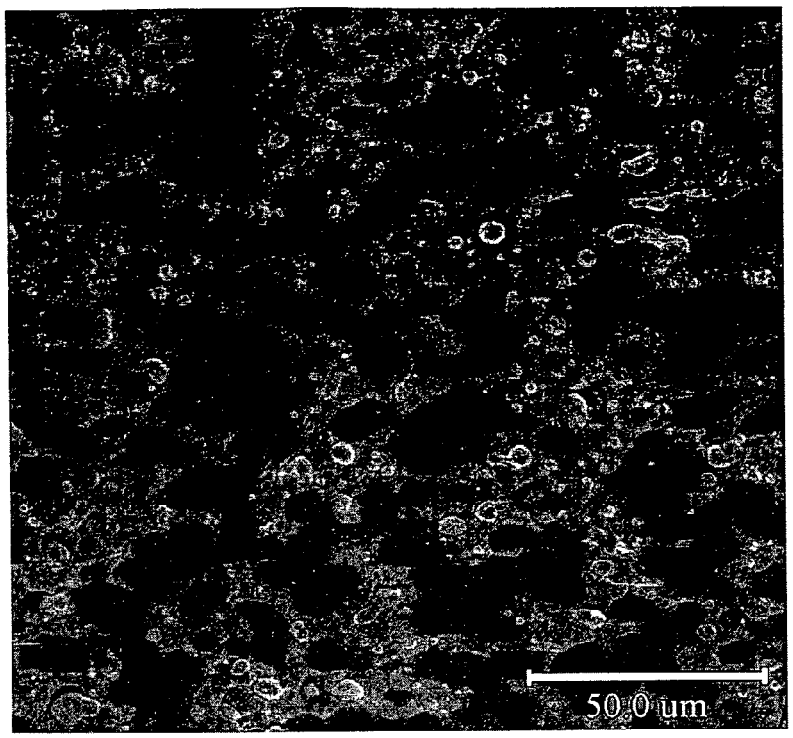
Figure 13. Surface micrograph of sensing electrode/diffusion barrier for sensor produced by the three-layer technique.

Figure 17. Sensors produced by the 5-layer technique with concentric pressing modification.
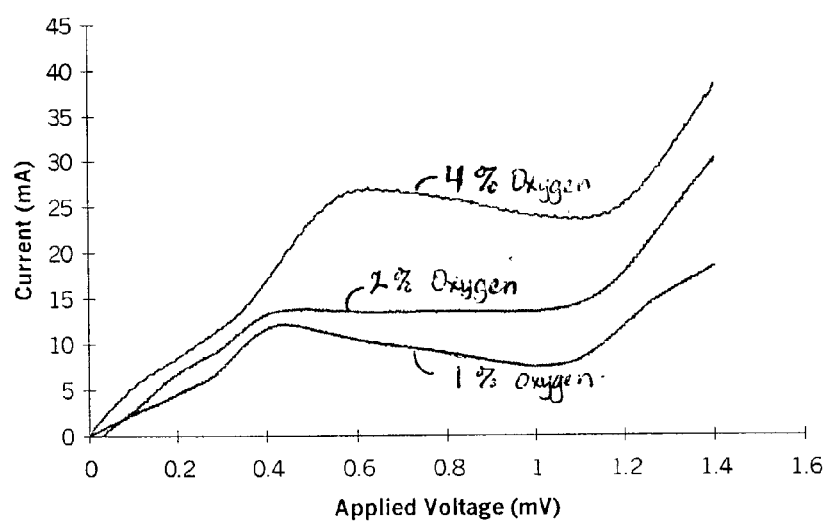
Figure 14. Voltage sweep on sensing electrode showing the wide sensor response region for 0 to 4 percent oxygen from 0.7 to 1.0 volts

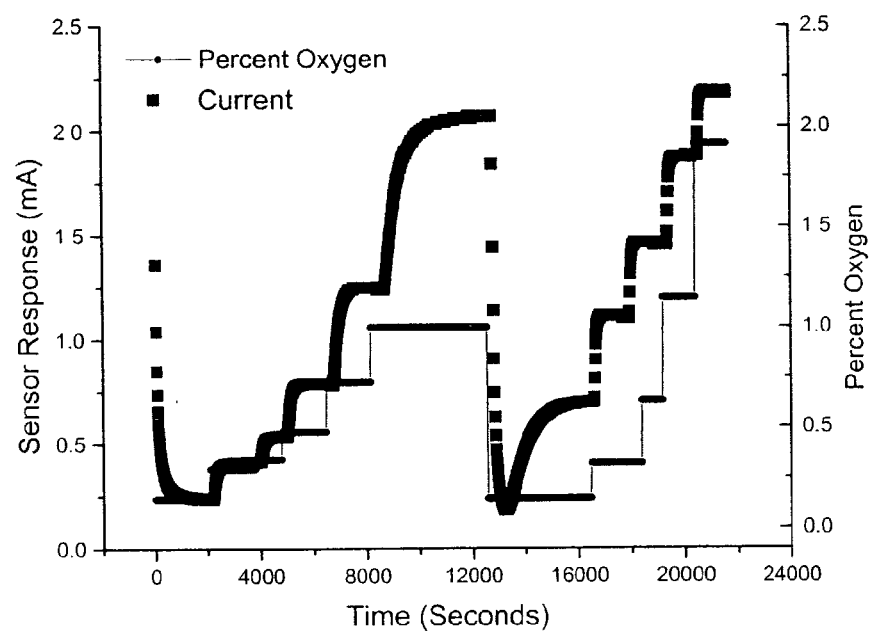
Figure 15. Sensor response to oxygen concentrations in the range of 0 to 2 percent.

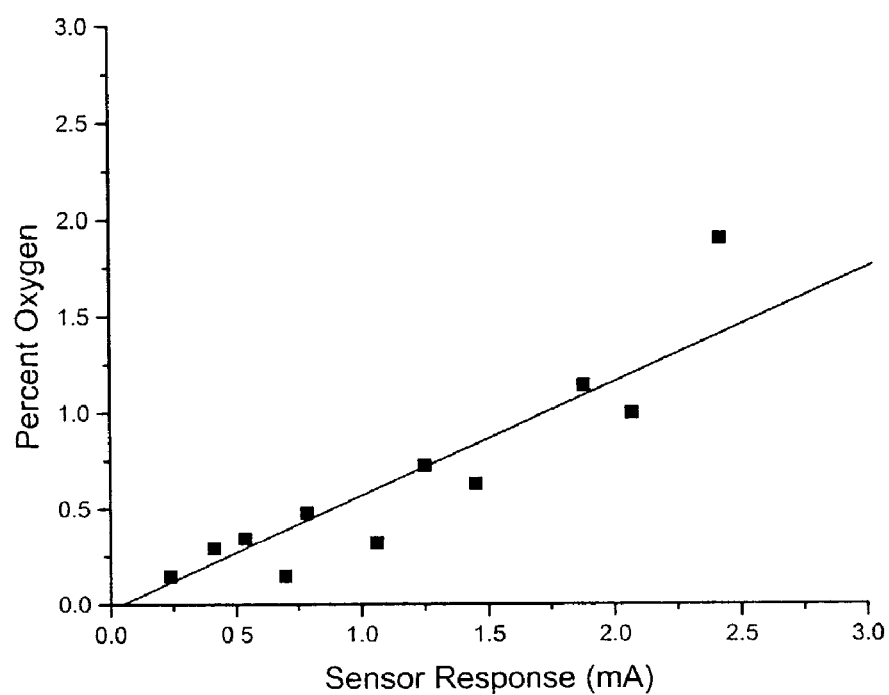
Figure 16. Linear sensor response for sensor produced by three-layer technique.

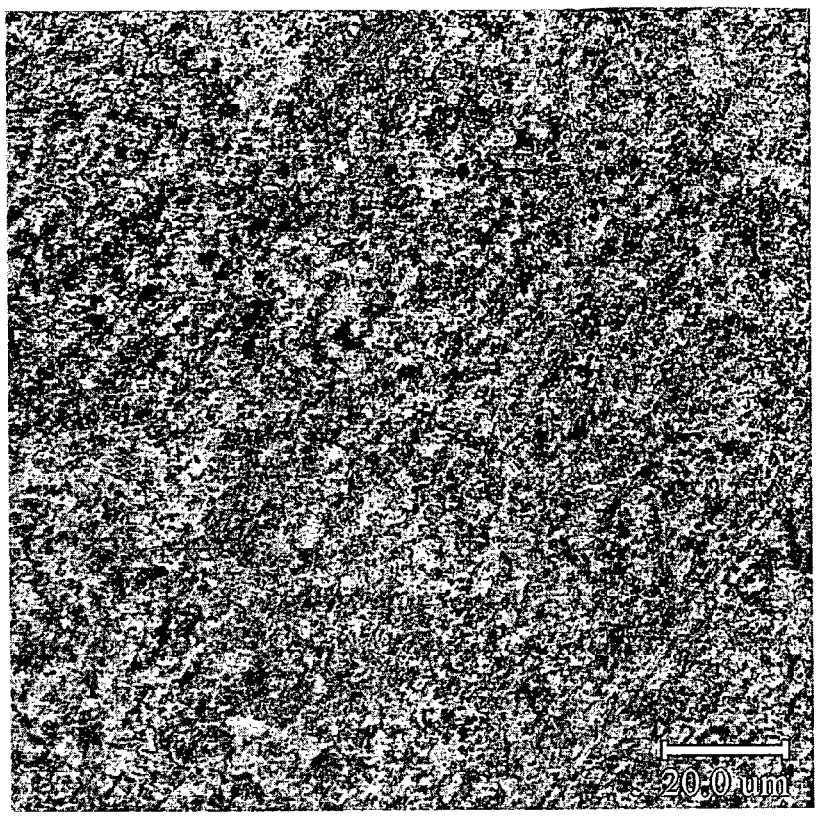
Figure 18. Surface of the diffusion barrier/sensing electrode of a sensor produced using the 5-layer technique.

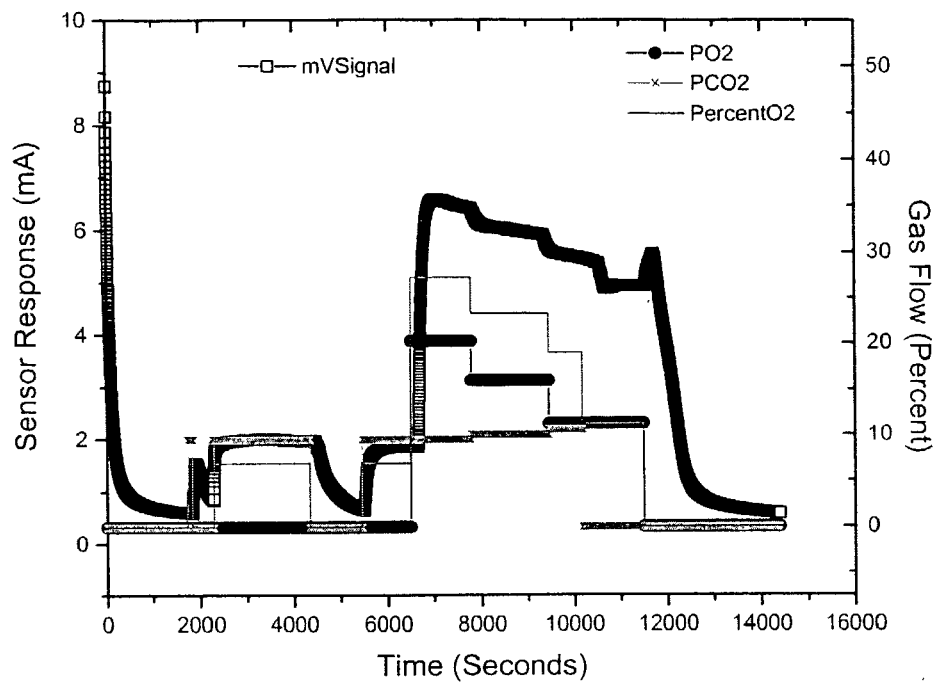
Figure 20. Response of 5-layer sensor to $CO_2$ and mixed $O_2$-$CO_2$..
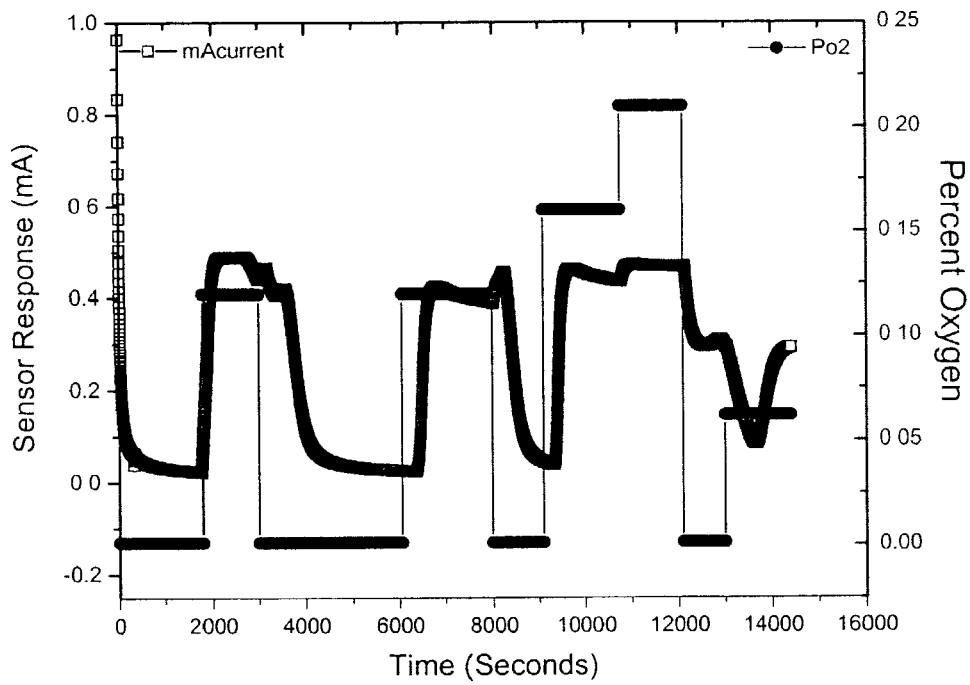
Figure 19. Response of sensor produced by 5-layer technique to oxygen.

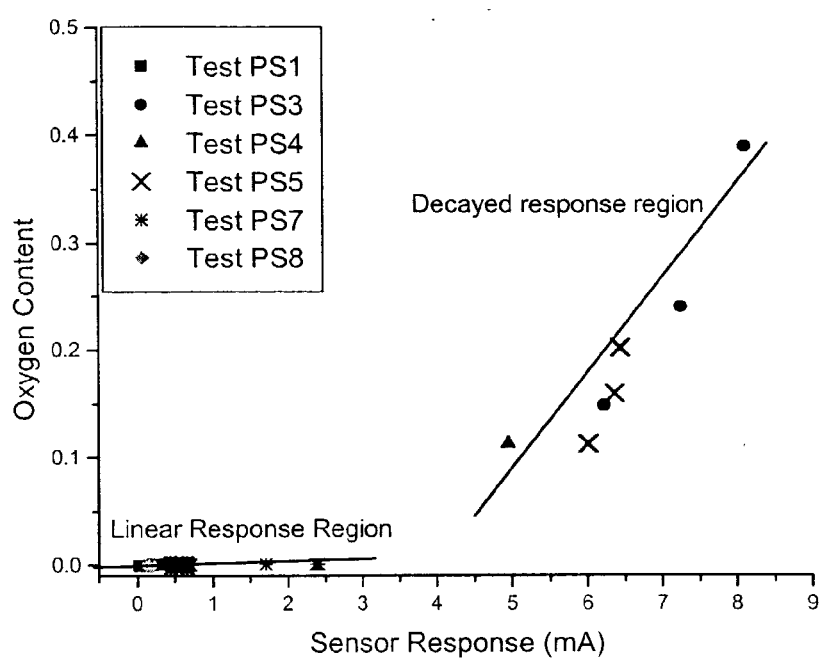
Figure 21. Total sensor response for 5-layer sensor including the linear regime and the saturation regime.

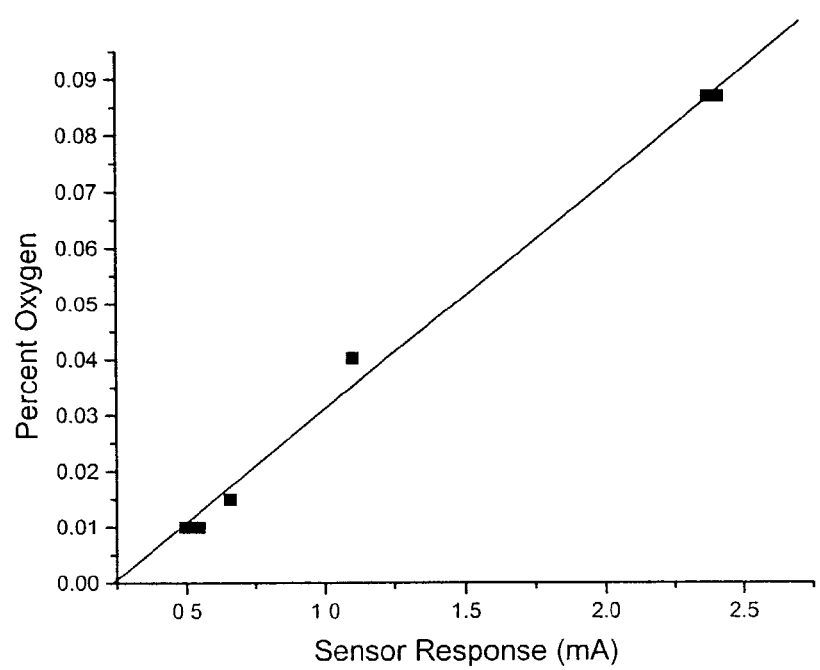
Figure 22. Linear response region of sensor produced using 5-layer technique.

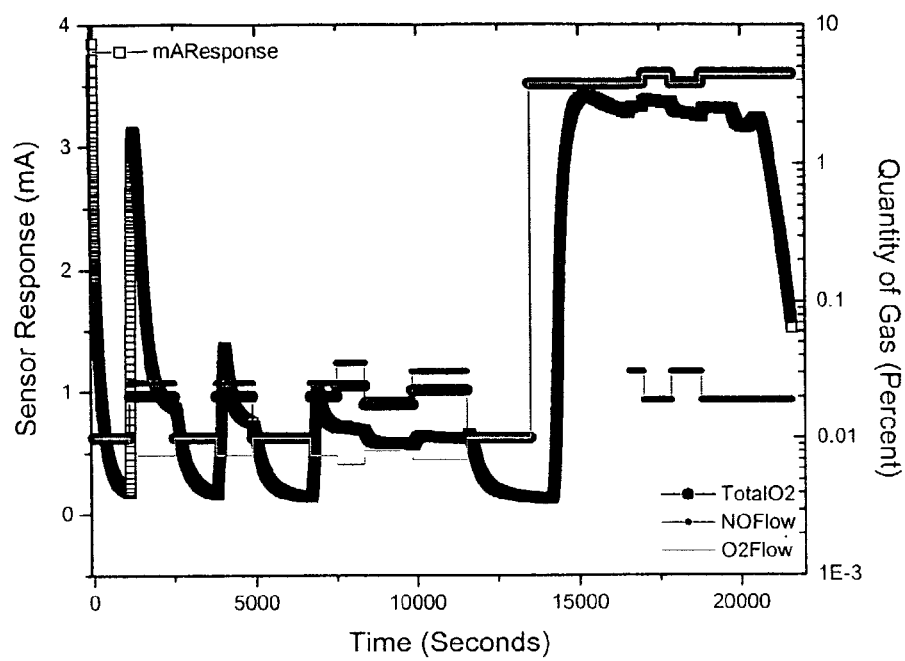
Figure 23. Response of 5-layer sensor to nitric oxide in the range of 0 to 400 ppm with and without additional oxygen.

OXYGEN SENSOR AND EMISSION CONTROL SYSTEM

This application is a continuation-in-part of U.S. utility application entitled, "Oxygen Sensor and Emission Control System," having Ser. No. 09/453,283, filed Dec. 2, 1999, now U.S. Pat. No. 6,440,283, which is based on and claims priority to U.S. provisional application, Ser. No. 60/110,628, filed Dec. 2, 1998, both of which are herein incorporated by reference.

TECHNICAL FIELD

The present invention is generally related to oxygen sensors, and, more particularly, systems and methods for measuring the concentration of oxygen in a flow of gas.

BACKGROUND OF THE INVENTION

Gas sensing is an important science with broad reaching implications throughout society. Gas sensors are used to monitor gas levels for safety, environmental impact and process control. Two economically important sensor types are for monitoring of household pollutants, such as carbon monoxide or explosive hydrocarbons, and oxygen sensors for combustion monitoring and control in automobile engines. The primary problem with oxygen sensors today is their lack of selectivity and limited sensitivity near lean burn conditions. These sensors primarily are based on a Nernstian response to oxygen partial pressure, and competitive surface reactions from many gases play a role in the sensor's response.

One approach to this problem is the use of amperometric sensors, which rely on the pumping of anionic oxygen species through an electrochemical membrane and measuring the associated electrical current through an electrical circuit. The advantage here is that the current measured has a direct linear relationship to the oxygen content in the gas, so long as the sensor is not overwhelmed by the overall oxygen gas concentration. In essence, the sensor must react with all interacting oxygen species in order to accurately count them. This mode is called the current-limiting mode for the sensor since the current measured is limited by the oxygen concentration. The best method of dealing with higher oxygen concentrations to date has been the diminishment of oxygen concentration near the sensor surface vis-à-vis a separate chamber, which is oxygen limited through the use of a diffusion limiting hole or separate oxygen pumping mechanism prior to the chamber. Neither of these prospects has received commercial recognition.

With continuous improvements and stringency in environmental regulations and advances in emission control technology, there is an intense demand for low-cost, high sensitivity gas sensors for better control of combustion in order to minimize pollutant emission while improving energy efficiency. One of the most important gas sensors is the solid-state oxygen sensor for control of the air-to-fuel ratio in automobiles, furnaces, and other combustion processes. While potentiometric oxygen sensors have been widely used for control of stoichiometric combustion, they are not adequately sensitive to changes in oxygen concentration when the partial pressure of oxygen in a sample gas is too close to that of a reference gas, typically air, because of the logarithmic response. On the other hand, an amperometric, or a limiting-current type, oxygen sensor exhibits a linear dependence on oxygen concentration in the sample gas. Amperometric sensors are, therefore, more suitable for control of lean-burn combustion.

For a traditional amperometric oxygen sensor, a porous ceramic layer, or a cap with a laser-drilled hole, is used as a diffusion barrier to control the inflow of oxygen. The characteristics of such a sensor depend critically on the microstructure of the diffusion barrier, or the size of the hole. The disadvantages associated with this design include: the pore or hole dimension is difficult to control; and (ii) the pores or hole can be readily blocked by particulates in the sample gas to be monitored.

To overcome these difficulties, mixed-conducting ceramic membranes have been used as the diffusion barrier for amperometric sensors, as described, for instance, in U.S. Pat. No. 5,543,025 to Garzon, et al. To date, however, the mixed conductors typically have been formed of lanthanum strontium manganese oxide (LSM), lanthanum strontium cobalt oxide (LSC), and terbia—yttria stabilized zirconia (Tb—YSZ). The stability of these mixed conductors is questionable and the reliability of a solid-state gas sensor depends mainly on the stability of the sensing components, particularly the one in contact with exhaust. For example, the stability and reliability of a sensor based on a mixed-conducting membrane may depend on the stability of the dense mixed-conductor membrane exposed to exhaust containing various pollutants at temperatures up to 1100° C.

It is well known that LSM and LSC are not very stable in gases containing unburned hydrocarbons and sulfur-containing compounds at high temperatures. These mixed conductors may undergo irreversible structural changes when exposed to unburned hydrocarbons. Further, they may readily react with sulfur-containing gases at temperatures up to 1100° C., forming reaction products at the surfaces that may alter the electrical properties of the materials. Accordingly, the performance of a sensor based on these mixed conductors may change during the course of operation, leading to drift in sensor output (or lack of stability), and even to sensor failure.

In addition to the chemical stability, the transport properties of the mixed conductors used as the diffusion barrier must not change significantly over the oxygen partial pressure range of interest in order to achieve wide-range oxygen detection. Unfortunately, the transport properties of LSM, LSC, and Tb—YSZ are known to change significantly with partial pressure of oxygen ($Po_2$), implying that sensors based on these materials may change sensing characteristics under these conditions. Further, these changes are often very slow, causing a slow drift in sensor responses. Therefore, it is desired that the mixed conductors used as the diffusion barrier have excellent stability under operating conditions to achieve stability, reliability, and reproducibility, and fast response.

Preparation of dense ceramic membranes on porous electrodes or substrates is an important step in fabrication of high-performance solid-state ionic devices or electrochemical systems such as solid oxide fuel cells (SOFCs), gas sensors, membrane reactors for gas separation or electrosysnthesis, and reformers for the processing of hydrocarbon fuels. In these applications, generally thin ceramic membranes are supported by porous substrates (or porous electrodes) since the electroactive species and the reaction products must be able to transport to or away from the surfaces of the dense ceramic membranes.

Various film deposition techniques have been explored for preparation of dense ceramic membranes on porous substrates, including a variety of atomic-scale physical and chemical vapor deposition, sol-gel process, electrochemical vapor deposition, combustion chemical vapor deposition, and more traditional particle deposition techniques. The atomic-scale deposition techniques involving a vapor phase or a solution often face difficulties either in stoichiometry control or in preventing the gas or the solution from filtration into the porous substrates. On the other hand, the particle deposition techniques such as electrophoretic deposition, colloid coating, screen-printing, tape casting, and tape calendering often have difficulties in achieving the required density or desired thickness. Further, and in particular, many of these film deposition techniques are complex, difficult to control, and expensive. In fact, it is the cost of fabrication that makes the commercial realization of many advanced technologies unaffordable. For example, while the existing SOFC technology has demonstrated much higher energy efficiency with virtually no pollutant emission over conventional energy technologies, the cost of the current SOFC systems is prohibitive for wide commercial applications. The cost of SOFC stacks is a major cost of fabrication.

Therefore, there is a need for improved oxygen sensors, systems and methods which address these and other shortcomings of the prior art.

SUMMARY OF THE INVENTION

The present invention is generally directed to an emission control system that includes an oxygen sensor. In a preferred embodiment, the sensor incorporates a diffusion barrier, an electrolyte material, and a counter-electrode. Preferably, the counter-electrode is configured to support the electrolyte layer, on which a diffusion barrier is deposited. In accordance with another aspect of the present invention, the present invention can also be viewed as providing a method for fabricating an oxygen sensor. In this regard, the method can be broadly summarized by the following steps: preparing a substrate, the substrate also serving as a counter electrode; preparing an electrolyte material; depositing the electrolyte on the substrate; preparing an organic film on the surface of the electrolyte; preparing a diffusion barrier, the diffusion barrier also serving as a sensing electrode; and depositing the diffusion barrier on the organic film.

In accordance with another aspect of the present invention, an alternative method for producing an oxygen sensor can be summarized by the following steps: preparing a diffusion barrier using sol-gel method, the diffusion barrier being a first electrode; pressing the diffusion barrier into a pellet; depositing mixed conducting oxide electrolyte powder on the diffusion barrier pellet followed by pressing; depositing a second electrode material onto pellet followed by pressing; and sintering of the diffusion barrier, electrolyte and second electrode to form a tri-layer oxygen sensor.

Other features, embodiments, and advantages of the present invention will become apparent to one with skill in the art upon examination of the following drawings and detailed description. It is intended that all such additional features and advantages be included herein within the scope of the present invention.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 6 represents graphs of I–V curves of a sensor (Pt/YSZ/Pt—YSZ) with counter-electrodes of different thicknesses prepared by brush painting, as measured in (a) 0.5% and (b) 3%, 6%, 9% and 12% $O_2$.

FIG. 7 is a flow chart of a preferred process for producing a preferred embodiment of the emission control system of the present invention.

FIG. 13 is a surface micrograph of the sensing electrode/diffusion barrier for a sensor of the present invention produced by the three-layer pressing technique.

FIG. 14 is a graph of the voltage sweep on the sensing electrode of the present invention, showing the wide sensor response region for 0 to 4 percent oxygen from 0.7 to 1.0 volts.

FIG. 15 is a graph of the response to oxygen concentrations in the range of 0 to 2 percent by the sensor of the present invention.

FIG. 16 is a graph of the linear response for a sensor of the present invention produced by the three-layer technique.

FIG. 17 is a top view of sensors of the present invention produced by the 5-layer technique with concentric pressing modification.

FIG. 18 is a surface micrograph of the diffusion barrier/sensing electrode of a sensor of the present invention produced using a five-layer technique.

FIG. 19 is a graph of the response to oxygen of the sensor of the present invention produced by the five-layer technique.

FIG. 20 is a graph of the response to carbon dioxide and mixed carbon dioxide and oxygen of the sensor of the present invention produced by the five-layer technique.

FIG. 21 is a graph of the total response to oxygen of the sensor of the present invention produced by the five-layer technique, including the linear regime and the saturation regime.

FIG. 22 is a graph of the linear response to oxygen of the sensor of the present invention produced by the five-layer technique.

FIG. 23 is a graph of the response of the sensor of the present invention produced by the five-layer technique to nitric oxide in the range of 0 to 400 ppm with and without additional oxygen.

DETAILED DESCRIPTION OF THE INVENTION

Figure 1:
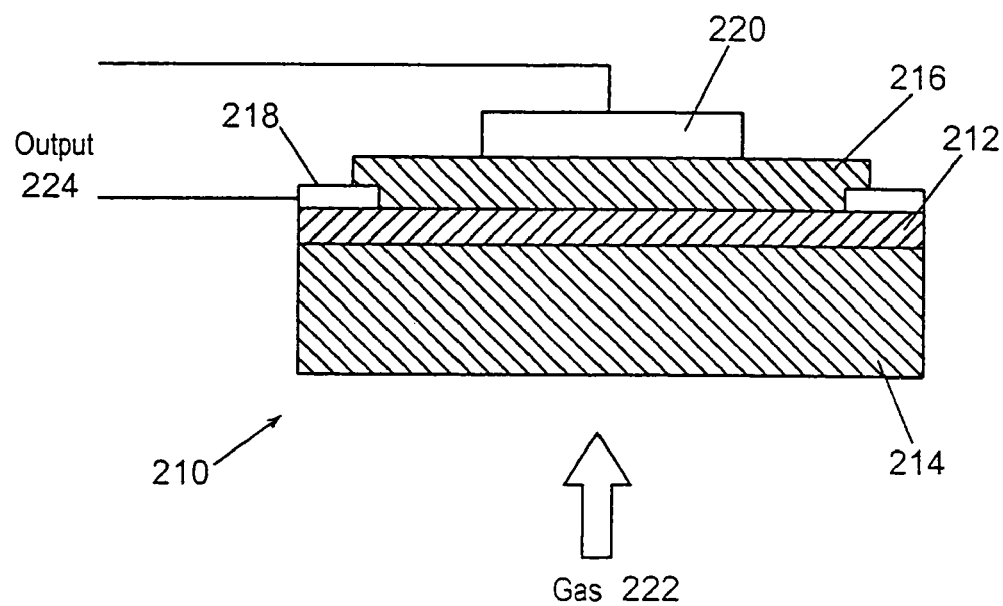
FIG. 1 is a side view of representative prior art sensor.

As described hereinbefore, prior art oxygen sensors typically contain a mixed-conducting ceramic membrane that is used as a diffusion barrier. One example of such a prior art sensor 210 is depicted in FIG. 1. The prior art sensor 210 includes mixed conductor 212 deposited on a porous substrate 214, which may be $Al_2O_3$, and a film of an electrolyte 216 deposited on the mixed layer conductor layer. Electrode pads 218, 220 are suitably deposited on mixed conductor 212 and electrolyte 216, respectively. Gas 222 containing an oxygen content is sampled through porous substrate 214 and a current plateau output 224 is provided. It will be understood that the position of electrolyte 216 and mixed conductor 212 may be reversed, whereby gas 222 is incident directly on mixed conductor 212. Many of the problems and deficiencies of the prior art sensor (mentioned hereinbefore) have been remedied by the present invention.

Figure 2:
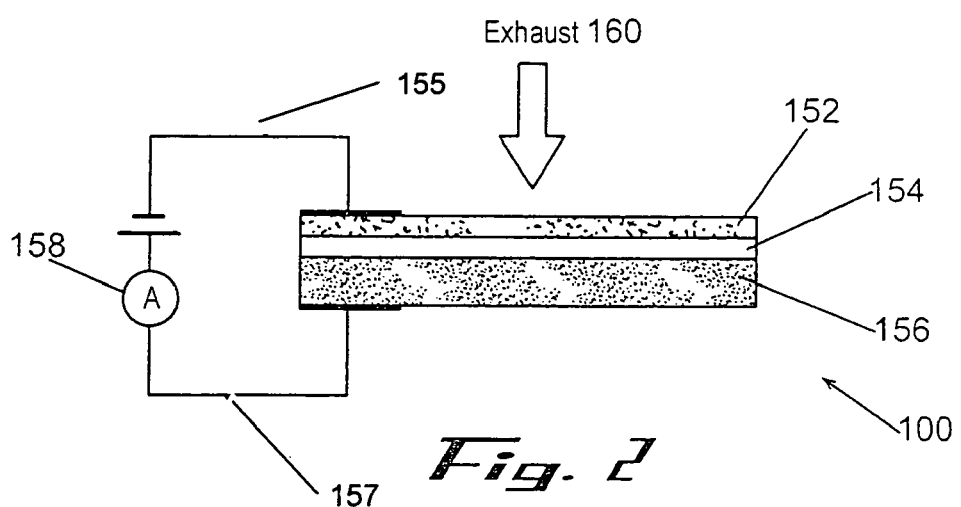
FIG. 2 is a side view of a preferred embodiment of the present invention.

As depicted in FIG. 2, a preferred embodiment of sensor 100 of the present invention incorporates a diffusion barrier 152, and electrolyte material 154, and a counter electrode 156, with the counter electrode 156 being configured to support the diffusion barrier 152, and the electrolyte material 154 being disposed between the diffusion barrier 152 and the counter-electrode 156. Preferably, wires 155 and 157 are provided which are connected to a monitoring system 158. As depicted in FIG. 2, the sensor 100 may be positioned within a flow of gas, such as exhaust 160, with the exhaust 160 being brought into contact with the diffusion barrier 152, for example.

A preferred embodiment of the present invention uses a dense composite membrane consisting of platinum and yttria-stabilized zirconia (YSZ) as the diffusion barrier 152 for amperometric oxygen sensors because of its high chemical and microstructural stability. To simplify the structure, a preferred embodiment of the present invention uses porous lanthanum strontium manganese oxide (LSM) both as a substrate to support the electrolyte film 154 and as the counter and/or reference electrode 156 for sensor 100 operation and measurements. Because the LSM will be exposed to a reference gas (air), and not to the exhaust 160, the LSM should be adequately stable under the operating conditions. Porous LSM has been used as a cathode for solid oxide fuel cells operated at 1000° C. for more than five years without significant degradation, demonstrating the longterm stability of LSM in air at 1000° C. Thus, in comparison to prior art sensors, the porous supporting substrate, i.e., porous alumina, is eliminated, and the Pt counter electrode is replaced with LSM electrode. The stability and performance characteristics of amperometric oxygen sensors 100 based on a Pt—YSZ composite membrane are discussed hereinafter.

In order to validate the successful implementation of the present invention, the following experiments were conducted.

Preparation of Electrolyte Pellets $La_{0.9}Sr_{0.1}Ga_{0.2}Mg_{0.8}O_3$ (LSGM) and YSZ were studied as an electrolyte 154 for the amperometric sensors 100. LSGM samples were prepared as described in F. Chen and M. Liu, *Transition Metal Oxides Doped LSGM as Electrodes for LSGM Electrolytes*, J. Solid State Electrochem, 3 (1998) 7–14. Stoichiometric amounts of $La_2(CO_3)_3 \cdot x\ H_2O$, $Ga_2O_3$, $SrCO_3$ and MgO were ball-milled in ethanol for 24 hours and calcined at 1300° C. in air for five hours. X-ray powder diffraction with a Philips PW 1800 was used to examine the phase composition of the calcined product. In case of incomplete calcination, ball-milling and calcination were repeated until pure perovskite phase was obtained. Powders with perovskite phase were crushed using agate mortar and pestle and then ball-milled in ethanol for another twenty-four hours. The resulting fine powder was pressed into pellets of 20 mm diameter and thickness of 2–3 mm. The pellets were sintered at 1450° C. for ten hours to get the dense LSGM pellets. Similarly, powder of yttria-stabilized zirconia, available as TZ-8™ from Tosoh, was pressed to pellets using the same die and sintered at 1350° for five hours. The microstructures of prepared pellets were characterized using a scanning electron microscope (SEM), Model Hitachi 5800. To measure the electrical properties, both surfaces of each sintered LSGM and YSZ pellets were grounded and ultrasonically cleaned before a paste of Pt electrode was screen-printed on them. Pellets with printed Pt electrodes were then fired at 820° C. for ten minutes to form porous Pt electrodes.

Preparation of Fine Platinum Powders and Pt—YSZ Mixed Powder

In a typical experiment, 20 g Pt powder available from Engelhard Corporation was dissolved into 120 ml HCl/$HNO_3$, with a volume ratio of 3:1, to obtain a clear $PtCl_4$ solution with dark orange color, which was then kept at 80 to 90° C. until its volume was reduced to about 80 ml. To this solution, 30 g polyethylene glycol, commercially available as PEG, F. W. 20,000, Alfa Chemical Company, was added under stirring at 80 to 90° C. until a viscous gel was formed, which was then dried using an infrared lamp. The dried gel was ground into powder and fired at 500° C. for two hours to obtain nano-particles of platinum. Alternatively, the prepared $PtCl_4$ solution, yttrium nitrate, commercially available as $Y(NO_3)_3 \cdot 6H_2O$, from Johnson Matthey, and zirconium dichloride oxide, commercially available $ZrOCl_2 \cdot 8H_2O$ from Alfa Chem Co. were used as precursors to prepare fine Pt—YSZ composite powders using a sol-gel process. Calculated amount of precursors were dissolved into water and appropriate amount of citric acid and PEG were added to this solution, which was stirred until it became clear. The molar ratio of citric acid to metal ions was 2:1. The PEG was approximately 50% of the weight of the metal and the metal oxide. The solution was then heated up to 80° C. to evaporate solvent and to obtain a gel, which was further dried using an infrared heating bulb. The dried gel was crushed into powders using agate mortar and pestle and followed by calcination at 650° C. for two hours to obtain Pt—YSZ composite powders.

The volume fraction of each phase in the Pt—YSZ composite must be appropriate in order for the layer to function as a mixed-conducting membrane. For a three-dimensional, two-phase composite mixed ionic-electronic conductor (MIEC), like Pt—YSZ, the percolation threshold is found at about one-third the volume fraction of the more conductive phase, Pt. The ambipolar conductivity is relatively high when the volume fraction of each phase is in the range of one-third to two-thirds so that both phases are continuous. Accordingly, the volume fraction of Pt in the composite was selected to be 40%. Because the density of platinum is 21.45 g/cm$^3$ and the density of YSZ is 5.89 g/cm$^3$, the weight ratio of Pt to YSZ was chosen to be 2.43.

Preparation of YSZ/Pt—YSZ Two Layer Structures Using Uniaxial Pressing

In a typical preparation, 5.000 g YSZ powder, available commercially as TZ-8Y™ from Tosoh, was mixed with 1.000 g PVA solution, 5 wt % in water, and ground until the binder was dispersed uniformly. In another mortar, 1.000 g Pt, sol-gel powder, was mixed with 0.412 g YSZ and ground in ethanol for 60 min to ensure uniform mixing, followed by the addition of 0.245 g PVA solution, 5 wt % in water, and ground for another ten minutes. First, 0.200 g YSZ-8 was put in die, and then the piston was turned back and forth for three to four times, followed by repress at 0.4 ton for three seconds. Then, 0.100 g Pt—YSZ was spread on the top of the repressed YSZ in die, the piston was turned back and forth for several times to make sure the Pt—YSZ powder is uniform and covers the surface of re-pressed YSZ completely. Finally, the powder was pressed at three tons, holding for 20 seconds to obtain a pressed two-layer pellet, which was then set on YSZ powder and sintered at 1630° C. for five hours.

Electrical Characterization

A computerized impedance analysis system, consisting of a Frequency Response Analyzer, Solartron 1255 and an Electrochemical Interface, Solartron 1286, was used to measure the impedance of the cells in air at temperatures varying from 600 to 800° C. in the frequency range from 65000 Hz to 0.1 Hz. The sensors 100 were tested in a tube furnace and the composition of sample gases was analyzed using an on-line gas chromatography (GC).

Results and Discussion

Microstructure of Powder and Pellet Electrolytes

An SEM view of the prepared LSGM powder, calcined at 1300° C. in air for five hours, indicated that the average particle size is about 1.4 µm. The surface view of an LSGM pellet sintered at 1450° C. for ten hours indicated that the sintered density was greater than 97% of the theoretical value. An SEM view of the YSZ powder, as received from Tosoh Corporation, showed particle sizes of about 100 nm. The surface view of a dense YSZ pellet, pressed using the Tosoh powder and sintered at 1350° C. for four hours indicated that the average grain size is about 1.5 µm with sintered density close to 100%.

Figure 8:
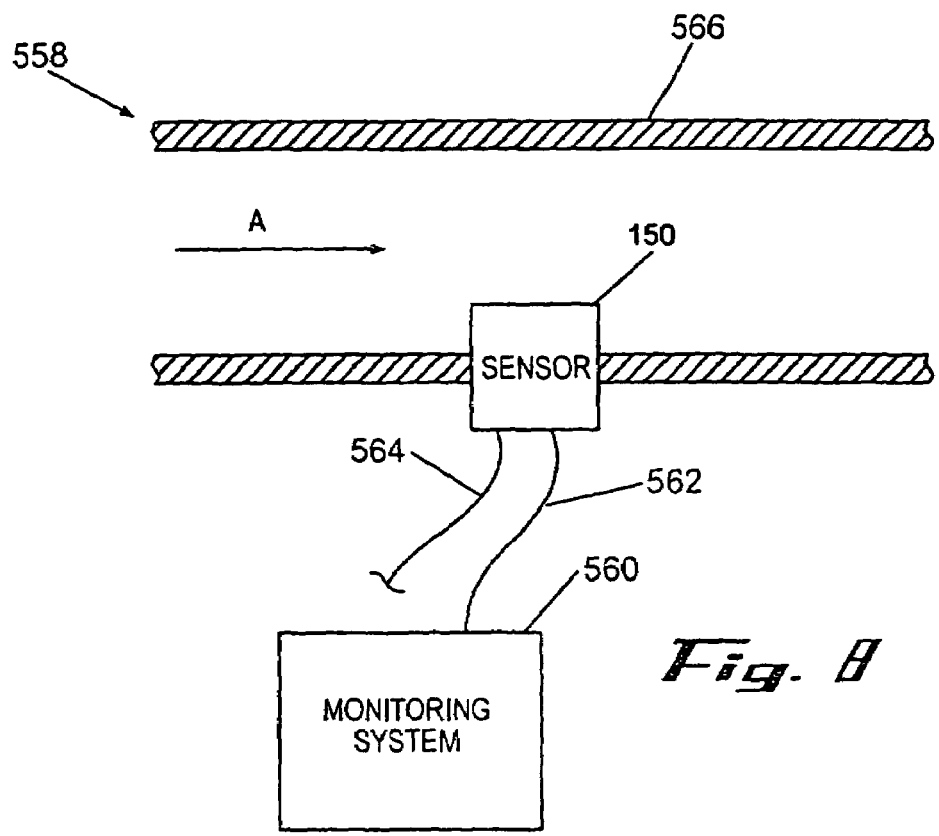
FIG. 8 is a schematic diagram depicting a preferred embodiment of the emission control system.
Figure 9:
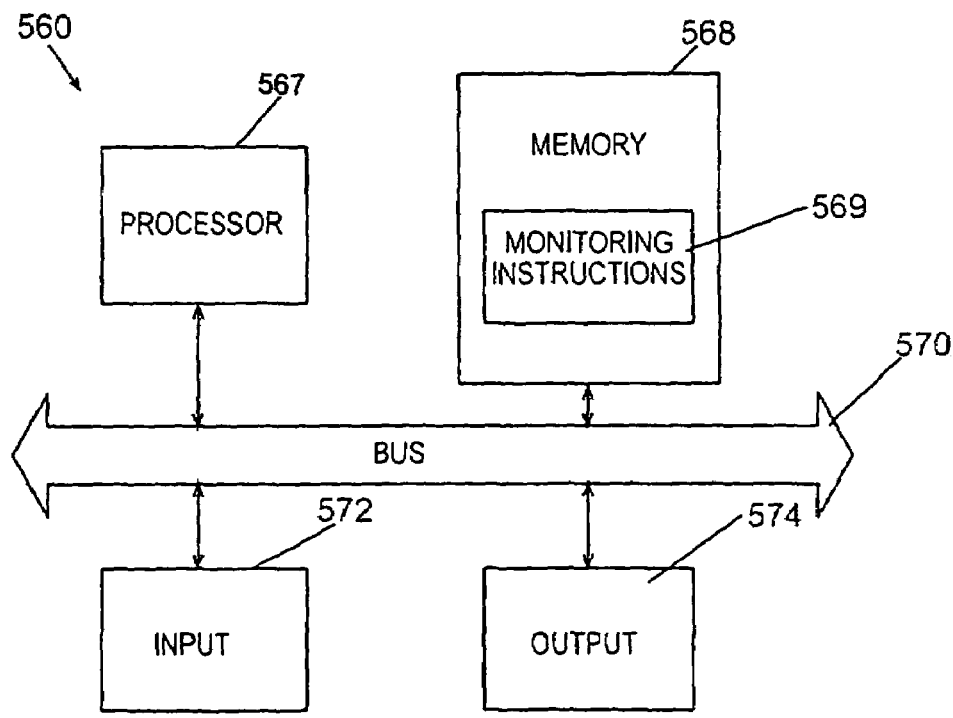
FIG. 9 is a schematic diagram of the monitoring system depicted in FIG. 8.

FIG. 9 illustrates a preferred embodiment of the monitoring system 560, i.e., a processor-based system, which may be utilized by the present invention. As shown in FIG. 9, the monitoring system 560 generally comprises a processor 567, a memory 568. Herein, the memory 568 may be any combination of volatile and nonvolatile memory elements, such as random access memory or read-only memory. The monitoring system 560 monitors the amount of oxygen detected by the sensor. The processor 567 accepts monitoring 569 instructions and other data from memory 568 over a local interface 570, such as a bus(es). The monitoring system 560 also includes an input 572, such as wire 562 (FIG. 8), and an output 574, such as a display, for instance.

Stability of the Electrolytes

Figure 3:
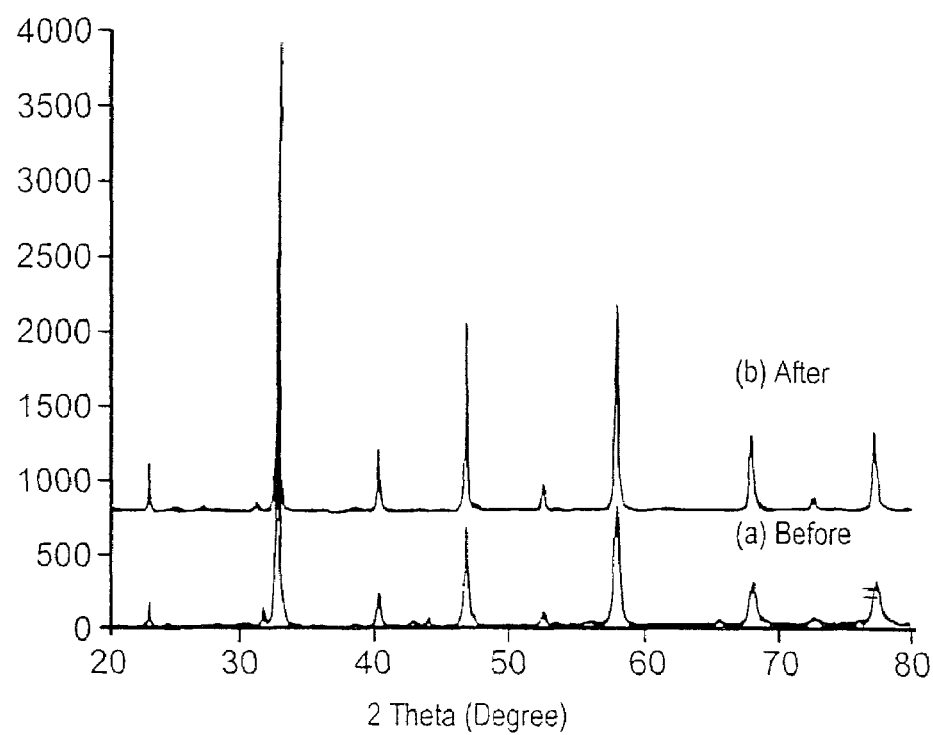
FIG. 3 is a graph of the XRD pattern of an LSGM sample (a) before and (b) after exposure to the exhaust of a gas-fired engine with a thermal history of fifty hours at 820° C., ninety hours at 840° C., and ten hours at 850° C.
Figure 4:
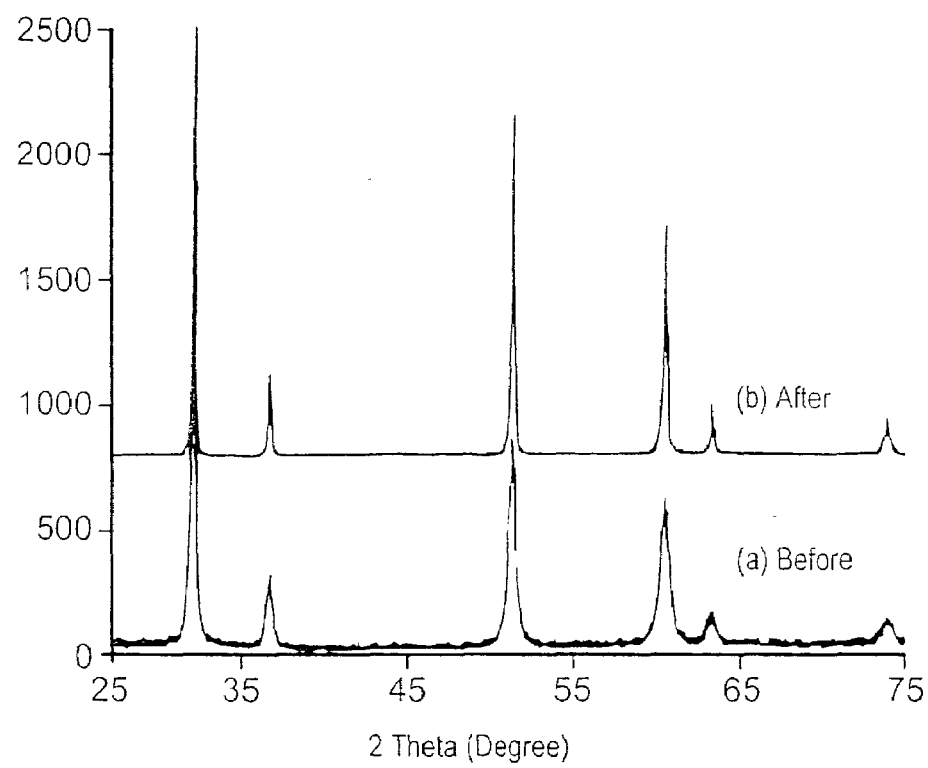
FIG. 4 is a graph of the XRD pattern of YSZ-8 (a) before and (b) after exposure to the exhaust of a gas-fired engine with a thermal history of fifty hours at 820° C., ninety hours at 840° C., and ten hours at 850° C.
Figure 5:
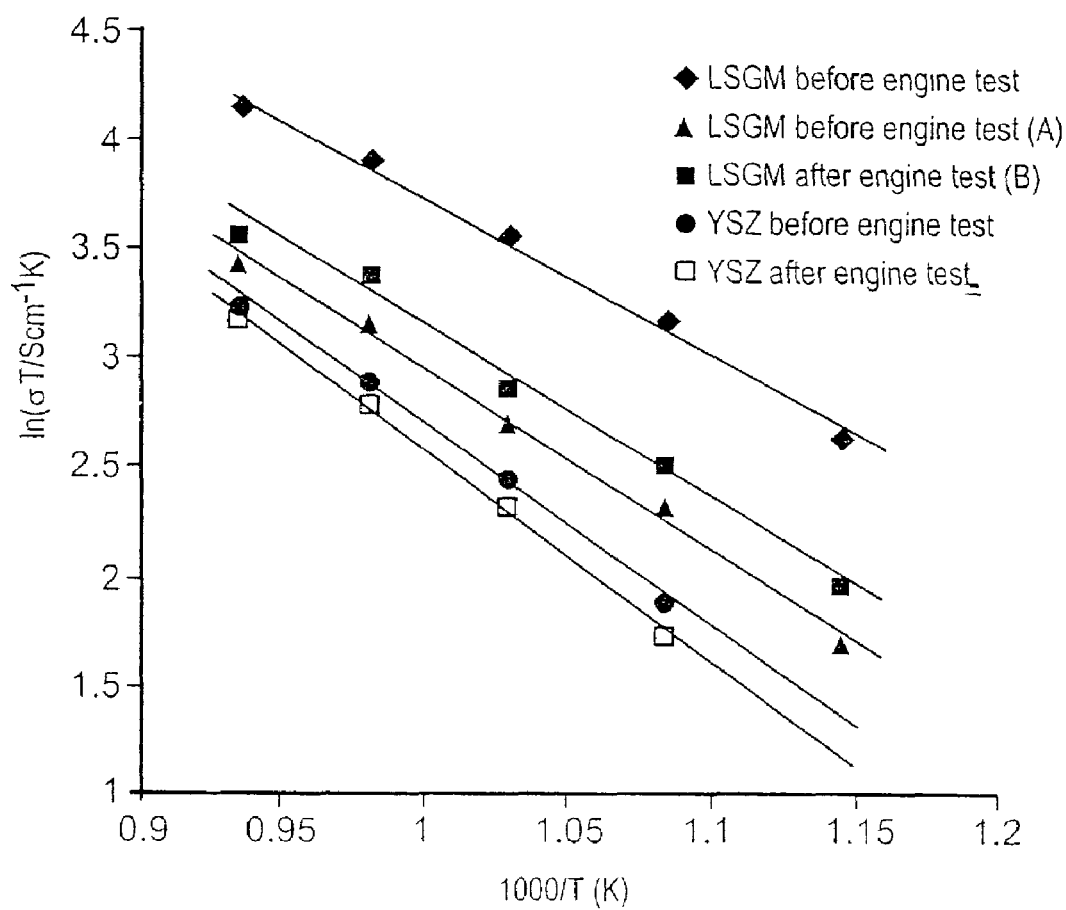
FIG. 5 is a graph representing the conductivities of YSZ-8 and LSGM samples (a) before and (b) after the engine-aging test as calculated from the impedance spectra measured at different temperatures.
Figure 1:
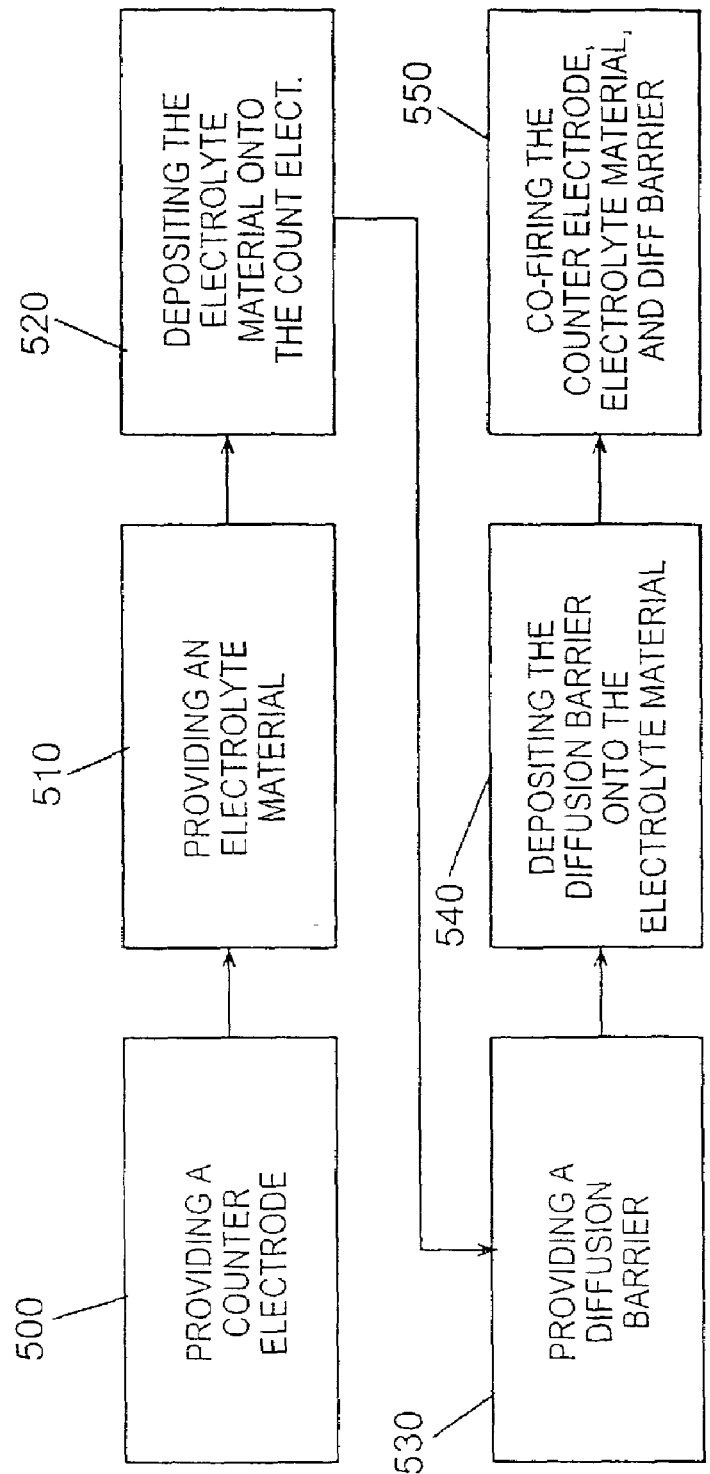

To study the stability of the electrolyte materials 154 for the sensor 100 applications, LSGM and YSZ samples were immersed in the exhaust of a gas-fired engine operated at stoichiometric combustion with a thermal history of 50 hours at 820° C., 90 hours at 840° C., and ten hours at 850° C. From the XRD patterns of LSGM and YSZ pellets before and after the aging test, as shown in FIGS. 3 and 4, respectively, it appeared that there were no observable phase changes for both LSGM and YSZ samples. The impedance spectra of LSGM samples before and after the aging test were measured at different temperatures in air and the conductivities of LSGM and YSZ, calculated from the impedance data are summarized in FIG. 5. Clearly, the conductivities of YSZ are within experimental error while the conductivities of LSGM indeed degraded considerably during the aging test, as shown in FIG. 5, respectively, implying that the stability of LSGM for the sensor 100 applications may be questionable.

Microstructure of the Composite Layer

The sol-gel derived Pt powder, available from Engelhard Corporation, is very uniform and the average particle size is about 100 nm. The particle size of the Pt powder from Engelhard varies from 0.1 to 0.6 µm. The platinum powders were mixed with Tosoh YSZ powders to form YSZ/Pt—YSZ bi-layer structures. The cross-sectional views of the two samples showed that the Pt—YSZ composite layer using sol-gel derived platinum powder is reasonably dense, whereas that using coarse platinum powder is porous.

Sensor 100 Performance

In determining sensor 100 performance, some typical I–V curves measured in different oxygen concentrations for a sensor 100 with configuration of Pt/YSZ/Pt—YSZ are shown in FIG. 6.

The diffusion-limited currents are flat for oxygen concentrations up to 12%. The diffusion-limited current, measured at 1 Volt, depends linearly on the oxygen concentrations.

The flow chart of FIG. 7 shows a preferred method of manufacturing a preferred embodiment of the oxygen sensor 100 of the present invention. The process begins at block 500 where a counter electrode is provided. The process then proceeds to block 510, where an electrolyte material is provided.

Block 520 represents the step of depositing the electrolyte material onto the counter-electrode. In block 530, a diffusion barrier is provided. Block 540 represents the depositing of the diffusion barrier onto the electrolyte material. In block 550, the counter-electrode, electrolyte material, and diffusion barrier are co-fired.

As depicted in FIG. 8, sensor 150 may be incorporated into an emission control system 558. Preferably, sensor 150 is arranged within a conduit 566 in which a flow of gas is provided, such as in direction A. So configured, at least a portion of the gas contacts a surface of the sensor 150.

The monitoring system 560 can be implemented in hardware, software, firmware, or a combination thereof. In some embodiments, the monitoring system may be an analog gauge, for instance. In a preferred embodiment, however, the monitoring system preferably is configured as a special purpose computing apparatus for implementing logical functions. A monitoring system 560 is attached to the sensor 150, preferably, by means of wires 562.

The monitoring system can be embodied in any computer-readable medium for use by or in connection with an instruction execution system, apparatus, or device, such as a computer-based system, processor-containing system, or other system that can fetch the instructions from the instruction execution system, apparatus, or device, and execute the instructions. In the context of this document, a "computer-readable medium" can be any means that can contain, store, communicate, propagate or transport the program for use by or in connection with the instruction execution system, apparatus, or device. The computer readable medium can be, for example, but not limited to, an electronic, magnetic, optical, electromagnetic, infrared, or semi-conductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (magnetic), a read-only memory (ROM) (magnetic), an erasable, programmable, read-only memory (EPROM or Flash memory) (magnetic), an optical fiber (optical), and a portable compact disk read-only memory (CDROM) (optical). Note that the computer-readable medium could even be paper or another suitable medium upon which the program is printed, as the program can be electronically captured, via for instance, optical scanning of the paper or other medium, then compiled, interpreted, or otherwise processed in a suitable manner, if necessary, and then stored in a computer memory.

Two general methods may be employed to realize an oxygen sensor 100 that operates in amperometric mode and utilizes a dense sensing electrode to create the diffusion barrier 152 that maintains operation in a current limiting mode over a wide range of oxygen partial pressures. The first technique involves the application of electrophoretic deposition of electrolyte 154 on a counter electrode 156, followed by the application of a combined diffusion barrier 152 and sensing electrode. The second technique takes advantage of the use of matched materials to create the entire sensor 100 in a single firing step. Two methods within the second technique can be used to achieve a layered structure including a counter electrode 156, an electrolyte 154 and a diffusion barrier/sensing electrode 152. The two techniques differ in starting materials and the particular processing used for the desired end results.

The amperometric sensor 100 of the present invention which has a sensing electrode which inherently places the sensor 100 in a current-limiting operating regime over a wide range of oxygen partial pressures without the use of a separate chamber with the associated diffusion hole or pumping mechanism. Generally, both amperometric and potentiometric (Nernstian) sensors 100 for high temperature applications are produced on ceramic membranes with highly porous metallic (usually platinum) electrodes for the express purpose of high efficiency. The concept presented herein of a dense electrode has been heretofore unrecognized in the art.

One design of a sensor 100 of the present invention involves a sensor 100 created on a counter electrode 156 support with a thin electrolyte 154 and a dense sensing electrode, which creates a current limiting condition due to the inherent inefficiency of dense electrode. The sensing electrode/diffusion barrier 152 is created using a sol-gel technique that creates a composite platinum—YSZ film that can be fired at low temperatures compatibly with the previously fired sensor substrate. The structure of the sensor 100 also incorporates an electrophoretically deposited electrolyte 154 supported by the counter electrode 156, whereas current and prior commercial sensors are supported by the electrolyte 154.

An alternative sensor 100 design includes a similar dense sensing electrode/diffusion barrier 152 through the use of more traditional processing. The method of the alternative embodiment is advantageous in that the diffusion limiting sensing electrode can be produced with even basic processing techniques. Two of these techniques for pressing involve the layering and pressing of multiple layers of ceramics in a manner that allows a co-firing process. The final product is a dense monolithic sensor 100 structure with high durability. A five-layer technique allows control of critical shrinkage and thermal mismatches in the material. Both the three-layer and five-layer techniques could be produced by a variety of ceramic processing techniques other than pressing, including tape casting, slip casting or co-extrusion. Co-fabrication and sintering of three sensor layers (counter electrode 156, electrolyte 154 and sensing electrode/diffusion barrier 152) with a single fire is included in the method of producing a sensor 100 of the present invention.

Figure 10:
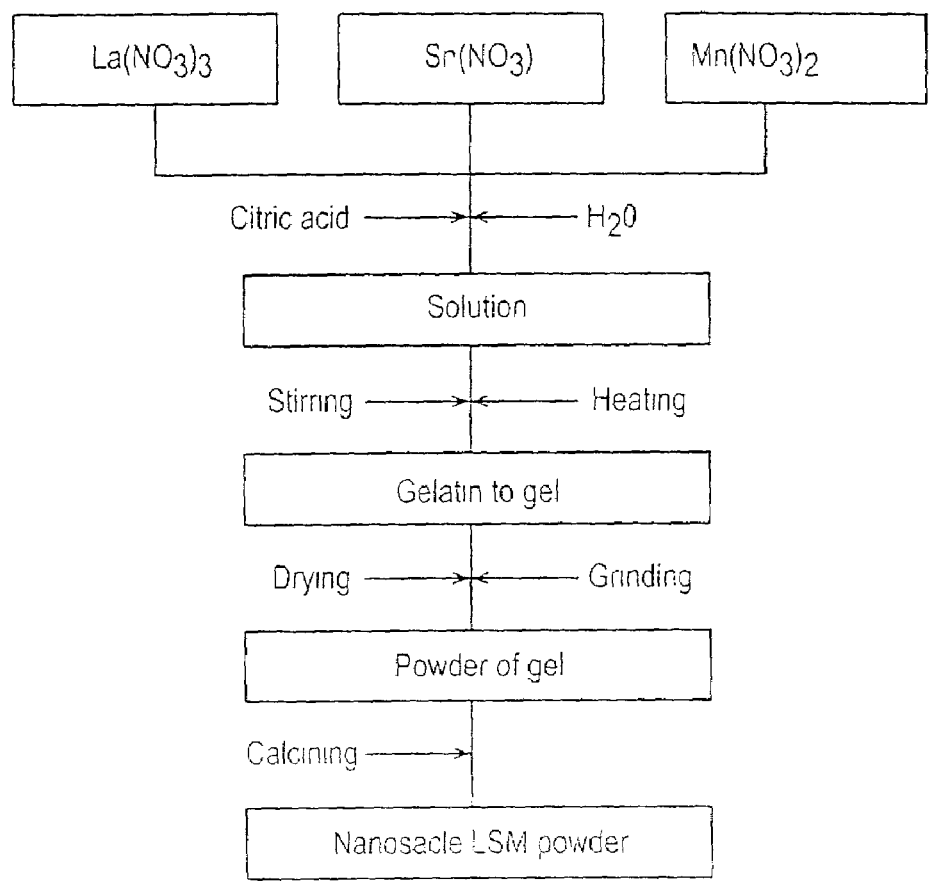
FIG. 10 is a flow chart depicting a preferred method for preparing fine LSM powders.

Method 1: Sol-Gel Synthesis a. Counter Electrode 156/Substrate Synthesis: Preparation of LSM Using a Sol-gel Process Schematically shown in FIG. 10 is a flow chart for the preparation of fine LSM powders. Stoichiometric amounts of $La(NO_3)_3 \cdot 6H_2O$ (99.99%), $Sr(NO_3)_2$ and $Mn(CH_3OO_2 \cdot 4H_2O)$ are dissolved in water, to which citric acid can be added under stirring. The molar ratio of metal ions to citric acid is preferably approximately 1:2. Once a clear solution is obtained, it is heated up to approximately 85–90° C. under continuous stirring to evaporate the solvent until gelation occurred. The gel is further dried using an infrared heater and then ground to powders, which are subsequently fired at different temperatures in air for different periods of time to get powders of different particle sizes. In order to increase the porosity of the LSM substrate, approximately 10% (weight) rice starch may be added to LSM powder, followed by ball-milling in ethanol for approximately twenty-four hours. After drying at approximately 80° C. under stirring, the powder can be pressed into pellets using uniaxial pressing; about 0.8–1 g for each pellet. These pellets may be used as the substrates for the deposition of the YSZ and Pt—YSZ films.

b. Electrolyte 154 Synthesis: Preparation of YSZ Films Using an EPD Method

Suspensions of YSZ powder can be prepared by dispersing YSZ powder (Tosoh TZ-8Y) and dissolving iodine in acetone. The reaction between acetone and iodine, $$CH_3COCH_3 + 2I_2 \rightarrow ICH_2COCH_2 + 2HI$$

produces protons which are absorbed on the YSZ particles, leading to positively charged YSZ particles. In fact, the zeta potential of YSZ particles in pure acetone is almost zero, but increases with concentration of $I_2$. Under the influence of an applied electric field, the ionic current passing through the suspension is carried not only by the charged oxide particles but also by free ions coexisting in the suspension. However, the amount of free ions is generally small in organic suspension such as acetone, so that the contribution of the free ions may be ignored. The weight (g) of charged particles deposited per unit area of electrode can be approximated by:

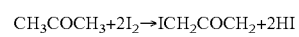

$$w = \tfrac{2}{3} C \epsilon_0 \epsilon_r \zeta \eta^{-1} E L^{-1} t$$

where C represents the concentration of the particles (g/L), $\epsilon_0$ the permittivity of vacuum, $\epsilon_r$ the relative permittivity of the solvent, $\zeta$ the zeta potential of the particle, $\eta$ the viscosity of the suspension, E the applied potential, L the distance between electrodes, and t the deposition time. Thus, the weight of deposited oxide particles, and hence the thickness of the oxide film, can be readily controlled through various deposition parameters.

Figure 11:
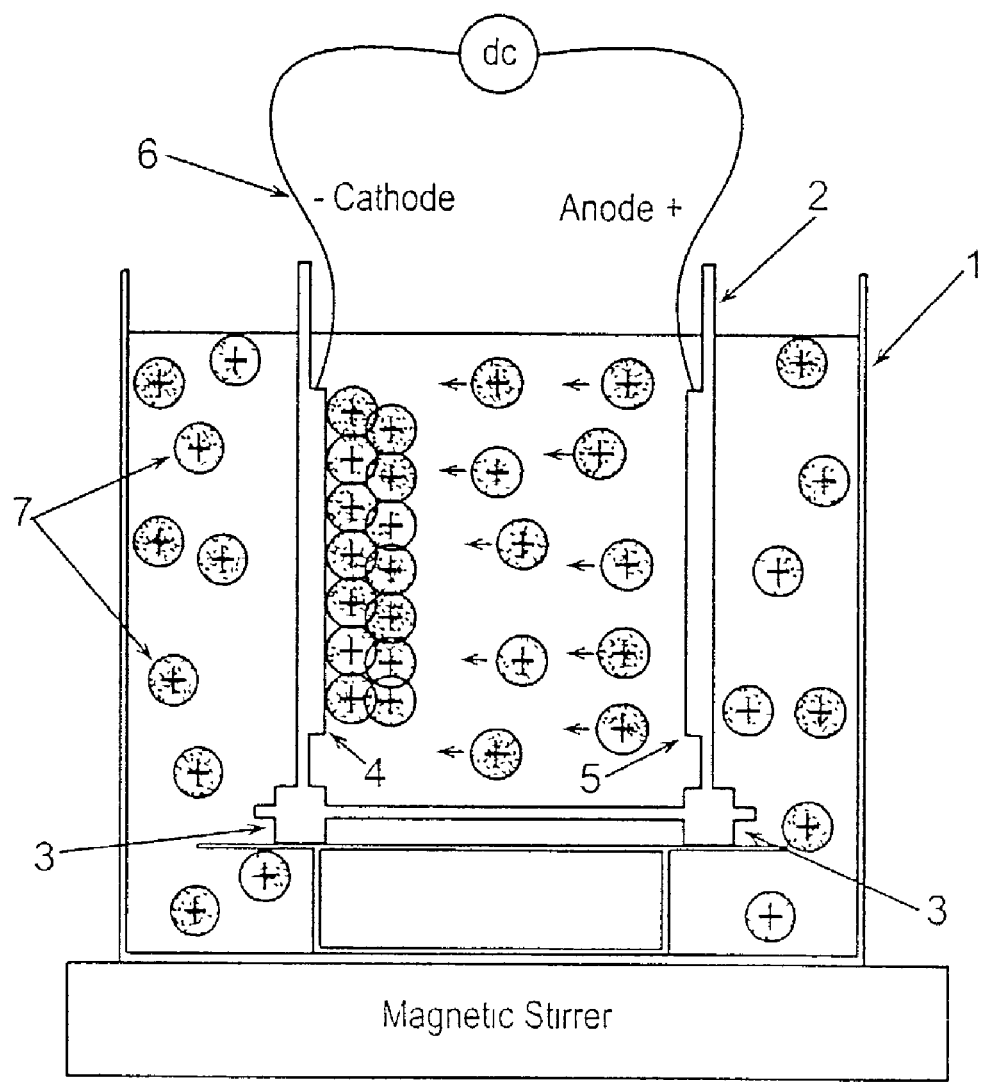
FIG. 11 is a cut-away side view of the experimental apparatus for the preparation of the YSZ thin film using an electrophoretic deposition or EPD process, with beaker 1, Teflon™ holder 2, screws 3, substrate (LSM pellet) 4, metal electrode (Pt disc) 5, wire 6, and charged YSZ particles 7.

Schematically shown in FIG. 11 is the apparatus used for deposition of YSZ film on LSM substrate using electrophoretic deposition (EPD). LSM substrate can be used as negative electrode, and a platinum disc used as the positive electrode. The concentration of $I_2$ and the concentration of YSZ powder in this suspension is preferably kept at 0.5 g/L and 10 g/L, respectively. The applied voltage between the two electrodes can be varied from 10 to 30 V and the deposition time varied from 5 to 30 minutes. It is desirable that the suspension be continuously stirred using a magnetic spin bar to maintain the uniformity of the solution during deposition.

c. Diffusion Barrier 152: Preparation of Composite Film of Platinum and YSZ (Pt—YSZ)

1. Colloidal deposition

Platinum ink (Engelhard) and Tosoh YSZ powder, of average particle size of about 0.1 μm are used to prepare colloidal solution of Pt—YSZ composite. A mixture of the Pt and YSZ may be dispersed for approximately 30 minutes in alcohol, and the weight ratio of solid to liquid is approximately 1:5, in the preferred embodiment, using an ultrasonic processor, GE 130, VWR, to obtain a colloidal solution. The colloidal solution is then deposited on the top of a green YSZ film, prepared using EPD, using a drop-coating or a spin-coating process, followed by drying at approximately 90° C. for approximately twelve hours and approximately 120° C. for approximately twelve hours.

2. Sol-gel process

An amperometric oxygen sensor 100 using a dense Pt—YSZ composite layer as a diffusion barrier 152 offers very high chemical and microstructural stability. To date, however, the sensors of this type were traditionally fabricated by uniaxial pressing. There are a few practical problems, though, with this fabrication method. First, the typical thickness of the Pt—YSZ layer is about 100–500 μm, making the sensor expensive, due to the amount of platinum used. Second, the pressed compacts are preferably sintered at approximately 1630° C. in order to achieve the required density. More importantly, the YSZ electrolyte 154 is too thick, approximately 500 μm, and it is functional only at high temperatures. The sol-gel process provides a solution to these problems.

To make an exemplary sensor diffusion barrier 152, approximately ten mg Pt powder, available from Engelhard, may be dissolved into a mixture of approximately 20 ml nitric acid and approximately 60 ml hydrochloric acid to form $PtCl_4$ solution, which is kept at approximately 80° C. until its volume is reduced to about 50 ml. The solution should darken. The concentration of Pt ions in the $PtCl_4$ solution is about 0.2 g/ml. Then, calculated amounts of $ZrOCl_2.8H_2O$ and $Y(NO_3)_3.4H_2O$ were dissolved in an appropriate amount of $PtCl_4$ solution.

The weight ratio of Pt to YSZ is preferably kept at approximately 3.5 to obtain a Pt—YSZ composite with approximately 40% (Volume) of Pt. It would be understood by one skilled in the art that other ratios are possible of Pt to YSZ. The obtained solution is preferably kept at 80° C. under stirring until its volume is reduced to half, in order to increase its concentration. Then, a polymer surfactant such as for example, but not limited to, polyethylene oxide (PEO) or polyethylene glycol (PEG) can be added to the solution to increase the viscosity of the solution and to maintain the uniformity of the gel films during drying. The amount of the polymer may be preferably about 10 wt % of the Pt and YSZ. The final solution is used to fill the pores in green Pt—YSZ composite films using a spin-coating process.

3. Preparation of polymer films.

Since the green Pt—YSZ and YSZ films are porous, the solution of Pt—YSZ may go through the YSZ film and filtrate into LSM substrate during the filling process, leading to electrical short between Pt—YSZ and LSM. In order to prevent this, an intermediate organic film without metal ions may be prepared on the surface of the porous green YSZ films before deposition of Pt—YSZ colloidal or sol solution. A suitable organic film for this purpose desirably has good wettability to the porous green films and to the Pt—YSZ sol solution. The organic film used may be produced as follows, as a mere example. Note, organic films other than those mentioned here may be suitable for use in as an intermediate layer in other embodiments of the present invention.

First, citric acid may be dissolved in ethylene glycol, with a molar ratio of ethylene glycol to citric acid of 3. The resultant mixture is then heated to 80° C. to promote polyesterification and resin formation. When the mixture becomes viscous, the solution is generally ready for coating.

After the organic film is prepared on the surface of green YSZ film, the sample sensor 100 may be subjected to drying at approximately 100° C. for approximately three hours. The Pt—YSZ colloidal and sol film are then deposited using a spin-coating method. This sample is then dried at approximately 80° C. for approximately three hours, followed by firing at, for example, approximately 500° C. for approximately thirty minutes with a heating rate of approximately 1° C./min from room temperature to approximately 500° C., to remove the organics. The Pt—YSZ solution filling and subsequent firing at approximately 500° C. can be repeated for a few more times as desired to increase the density of Pt—YSZ film. Finally, the sample is co-fired at approximately 1250° C. to obtain the dense Pt—YSZ/YSZ films on the porous LSM substrate. Although other polymers such as PEG and PVA may also used, they tend to cause cracking during drying at high temperatures, probably due to excessive shrinkage of the polymers.

Results and Discussion (Method 1)

Characteristics of LSM Powders and Porous LSM Substrates

Figure 12:
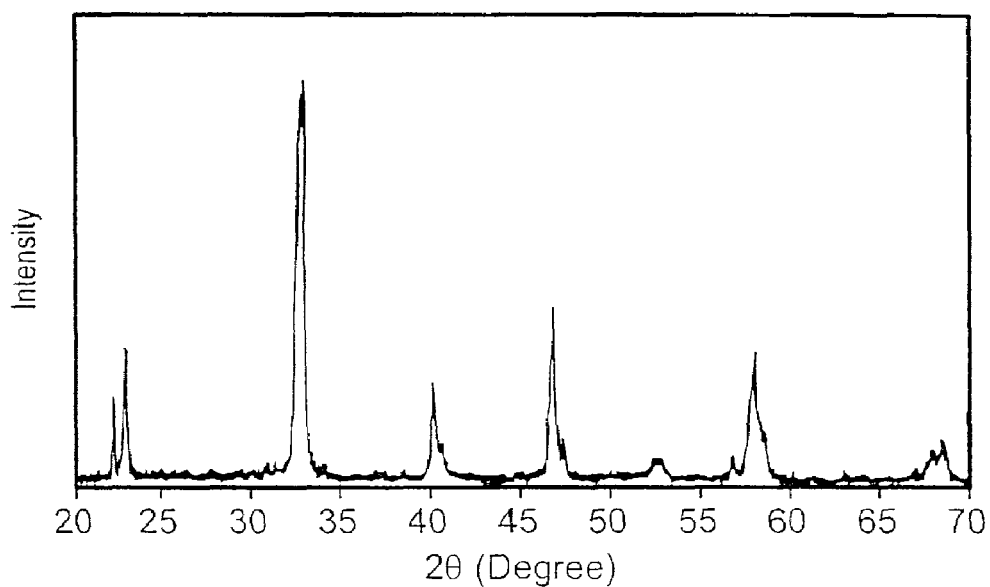
FIG. 12 is a graph of the X-ray diffraction pattern of the LSM powder, fired at 550° C. in air for three hours.

Shown in FIG. 12 is an X-ray diffraction (XRD) pattern of the LSM powder derived from a sol-gel process, implying that the LSM powder, fired at 550° C. for two hours, has a perovskite structure. This temperature is much lower than the calcination temperature needed to form perovskite LSM, which is about 800 to 1000° C., when a traditional ceramic process is used. A transmission electron microscope (TEM) micrograph of the sol-gel derived LSM powder indicated that the average particle size is about 40 nm.

The microstructure of LSM substrates sintered at 1150° C. and 1250° C. for three hours, respectively, showed that while the grain size of LSM increased dramatically during sintering, the final porosity of the substrate is about 36%, adequate for electrode applications. Large shrinkage of the LSM substrate also should be considered when using powders derived from the sol-gel method. Due to the small particle size and large amount of pore former, rice starch in the form of green pellets, the shrinkage of LSM substrates is about 23%, much larger than those prepared using a traditional ceramic process, which is about 17%. It is believed that this large shrinkage plays a role in assisting densification of the YSZ and Pt—YSZ film during sintering.

Microstructure of YSZ Film

The surface of the YSZ film produced by the instant process is smooth and uniform. Preparation of high quality green YSZ film aids in the preparation of dense YSZ film on porous substrate. The quality of YSZ green film is influenced by many process parameters. In particular, the concentration of the suspension, the applied voltage, and the deposition time are all parameters that influence the quality of the YSZ film. If the concentration of YSZ in the suspension is too high, the deposition rate of YSZ particles would be very fast, leading to poor packing density of the green YSZ film with pores or pinholes. The same is true when the applied voltage is too high. At a given concentration of YSZ in the suspension and an applied voltage between the two electrodes, the thickness of the green YSZ film is primarily determined by the deposition time. Typically, it is difficult to obtain a crack-free green film when the film is too thick.

Acetone has small surface tension but high evaporation rate; thus, it typically dries too fast when the film is taken out from the solvent, leading to cracks in the green YSZ films. Ethanol has slower evaporating rate, but its surface tension is larger than acetone, which leads to the sliding down of the YSZ film deposited on the surface of the porous substrate when the film is taken out from the suspension. In order to overcome these problems, a mixture of 75% V acetone and 25% V ethanol was used in this example.

The conductivity of LSM substrate is also a factor to consider during deposition of green YSZ film. Low conductivity of substrate can lead to non-uniform green film and slow deposition.

The microstructures of YSZ films on LSM substrates fired at different temperatures showed that while the film fired at 1150° C. for three hours is still porous, the film fired at 1250° C. for three hours is very dense. The thickness of the dense film is about 7.5 µm.

These results clearly demonstrate that dense YSZ thin films can be prepared on porous LSM substrate of sol-gel derived powder at temperatures as low as 1250° C., which is about 200° C. lower than other film deposition approaches reported in the prior art.

Microstructure of Pt—YSZ Composite Film

Several processes have been studied for the preparation of Pt—YSZ composite film. From an SEM micrograph, it can be seen that the YSZ layer is dense, the LSM substrate is porous, but the Pt—YSZ composite layer is not as dense as required for an amperometric sensor 100 using the Pt—YSZ as diffusion barrier 152. However, the structure is desirable for solid oxide fuel cells or other electrochemical functions where both electrodes must be porous.

Several factors may influence the density of the top Pt—YSZ layer. One possibility is that the platinum particle size may be too large. As discussed elsewhere, the composite includes coarse platinum powder and Tosoh YSZ is still porous after being sintered at 1630° C. for five hours while sol-gel derived platinum and Tosoh YSZ is completely dense under the same conditions. Thus, a combination of the colloidal and the sol-gel process was pursued to prepare dense Pt—YSZ composite films.

First, the surface of the YSZ film was coated with a blank polymer film as described earlier to prevent infiltration of Pt solution into the green YSZ film. Second, a colloidal solution of Pt—YSZ was deposited on the top of the polymer-coated YSZ film to obtain a Pt—YSZ film. Third, a sol-gel process was used to fill the pores in the colloidal film of Pt—YSZ using a Pt—YSZ solution. Finally, all layers on an LSM substrate were co-fired at 1250° C. for three hours to obtain dense YSZ and Pt—YSZ films on a porous LSM substrate.

It is clear from an SEM micrograph that the surface of the Pt—YSZ film is completely dense and pin-hole free. The cross-sectional views show that both YSZ and Pt—YSZ films are reasonably dense while the LSM substrate is still porous, a desired structure for an amperometric sensor 100. It is believed that the small particles from the PtYSZ solution not only reduce the porosity of Pt—YSZ colloidal film, but also improve the sintering behavior of the composite film. The small particles disposed among big colloidal particles may act as the bridge between large particles for mass transport and densification during sintering, resulting in reduced sintering temperature and increased density of Pt—YSZ composite films.

Method 2: Dry Pressing

One technique for dry-pressing utilizes a platinum produced from a modified sol-gel process combined with commercial yttria-stabilized zirconia to produce both the counter electrode 156 and the diffusion barrier/sensing electrode 152. Platinum powder is dissolved in mixed nitric and hydrochloric acid to produce a platinum chloride solution. To this solution is added citric acid and ethylene glycol. Upon heating, the solution evolves water and produces a gel. This gel is put through a combustion process to remove the organic material, leaving a very fine nanoscaled powder.

This powder is combined with Tosoh YSZ with a mortar and pestle to create the base material for the sensing and counter electrode 156. The composite powder contains in the range of approximately 30 to approximately 50 percent platinum which provides the electronic conduction required in the electrodes. The remaining approximately 50 to approximately 70 percent is composed of YSZ which creates ionic pathways through the electrode to the electrolyte 154.

a. Three-layer Fabrication

In the three-layer pressing technique, the platinum—YSZ composite powder is added into a cylindrical pellet die. The powder is initially pressed in the 10 mm die at approximately 1 ton of pressure. Next, Tosoh YSZ powder is added to the die to create the electrolyte layer 154. This is also pressed to approximately 1 ton of pressure. Finally, a thinner layer of platinum—YSZ powder is added to the die and pressed to approximately 2 tons of pressure, creating a three-layered structure.

Once removed from the die, the pellet is sintered to a temperature between 1550 and 1650° C. for approximately 4 hours yielding a solid dense monolithic cell. The use of nano-particles of platinum with fine YSZ creates a limited amount of phase boundary in the electrode regions. This limited triple-phase boundary minimizes gas interactions and allows the measurement of relatively high oxygen partial pressures with linear sensor response.

For the three-layer fabrication technique, the microstructure of the sensing electrode/diffusion barrier 152 is relatively coarse due to mixing difficulties of the YSZ and platinum powders for the composite layers. The microstructure is seen in FIG. 13. This produces very limited triple-phase boundaries in comparison with the traditional porous electrodes. Since the number of reaction sites is determined by the quantity of triple-phase boundaries, the sensor interaction may be limited by this microstructure.

Voltage sweep performed in atmospheres containing varying amounts of oxygen produce the results seen in FIG. 14. The sensor 100 gives clear current limiting response over the range of 1 to 4 percent oxygen. Operating at a fixed voltage, the sensor 100 responds quickly and predictably to changes in oxygen concentration as seen in FIG. 15. The linear relationship of the current response of a sensor 100 operated in amperometric mode under a bias of 0.8 volts is seen for a variety of oxygen concentrations in FIG. 16. Other sensors 100 produced by these techniques have shown linear response at oxygen concentrations of up to 10 percent.

b. Five-layer Fabrication

Five layer fabrication involves constraint during the firing process to eliminate warpage and produce a more ideally planar device. In particular, five-layer fabrication evolved as a response to working with a platinum—YSZ material that produced a finer microstructure but had very different firing shrinkage profile in comparison to the YSZ electrolyte 154.

The powder for the platinum/YSZ composite layer, the electrode layer 156, may be produced using a glycine-nitrate/precipitation hybrid technique. In this technique, platinum is dissolved in a mixed nitric/hydrochloric acid solution. This solution is added to zirconyl nitrate and yttrium nitrate solution, which is complexed with glycine. Nitric acid may be used because it provides an excess of oxygen for combustion of the glycine. Upon heating, the water begins to evaporate from the system, which causes a precipitation of $ZrO_2$ particles. With constant stirring, the $ZrO_2$ particles stay uniformly suspended while the glycine complex gels. The glycine complex contains platinum and yttrium ions which, when heated above 140° C., ignite to rapidly burn. The heat of combustion causes the zirconia particles to form a cubic crystal structure and a fine porous network, most likely due to the incorporation of yttrium ions and the platinum. The final powder is light, and contains both the YSZ and platinum phases incorporated into a fine mixture. A similar process can be performed without the platinum to yield extremely fine YSZ particles.

The intimate mixing and ultra-fine particles attained in material prepared for the electrode layer by this technique sinter to high density while maintaining a fine grain structure at lower sintering temperatures. However, due to differences in compaction and shrinkage during sintering compared to the previous method, these powders may create problems with warping and delamination during firing. To maintain a uniform sample geometry, a five-layer pressing technique has been developed to minimize these difficulties.

In the five-layer pressing technique, the first layer pressed is the center layer, electrolyte 154. A 13-mm die is loaded with YSZ powder and pressed to approximately two tons of pressure. The punches are aligned in the die to create this electrolyte layer 154 in nearly the center of the die. The punch from the bottom is carefully removed, and platinum—YSZ nano-composite powder is added. The punch is replaced and the powder is again pressed with two tons of pressure. The top punch is removed and the sequence is repeated for the top electrode. This process is then replicated once again for the top and bottom of the sensor 100, using pure or nearly pure YSZ powder. The final pressing occurs at 3 tons of pressure.

The pellet with its five pressed layers is removed from the die and sintered in the range of 1350 to 1500° C. The top and bottom YSZ layers contain the platinum—YSZ composite layers during firing and create a dense and flat sample. The top and bottom layers are ground off using abrasive grinding media to expose the sensing and counter electrode 156. These layers may be polished to high smoothness to create a surface which will not collect debris during operation or that will allow the application of a selectivity-enhancing layer.

A further enhancement of concentric pressing of the sensor 100 takes the above principles and expands them by using pre-pressed platinum—YSZ pellets, which are smaller than the sensor die (10-mm in a 13-mm die). The procedure then places the pre-pressed electrodes on the electrolyte and fills the circumference with YSZ powder. Pressing the electrode layers this way produces an edge-sealed sensing and counter electrode 156 to enhance the ability of the sensor 100 to be sealed at the edges, or to accept a semi-permeable selective coating on its surface.

Results: Five-layer Fabrication Method

The sensor 100 produced from the five-layer technique is uniform, dense, and due to the removal of the top and bottom layers, planar. FIG. 17 depicts sensors 100 produced using the five-layer technique with the concentric pressing enhancement. The sensor surface shows fine intermixing of the platinum and YSZ phases creating substantial triple-phase boundary (FIG. 18). This is primarily due to the fine structure and mixing occurring during the powder processing, but is aided by the ability to sinter the sensor 100 at lower temperatures than in the three-layer technique.

The sensor 100 is shown to respond to a variety of oxygen-containing gaseous species including oxygen and carbon dioxide, as seen in FIGS. 19 and 20, as well as nitric oxide. The response is only linear at low oxygen partial pressures for this sensor 100, as seen in FIGS. 21 and 22. The fine microstructure and enhanced triple-phase boundary are particularly suited for measurements at low oxygen concentrations where the sensor 100 can transport all oxygen species that interact on the sensor 100 surface. The response to nitric oxide at low concentrations is seen in FIG. 23, where the sensor 100 responds to changes in nitric oxide from 0 to 400 ppm with and without the presence of added oxygen in the system.

It should be emphasized that the above-described embodiments of the present invention are merely possible examples of implementations set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

What is claimed is:

1. A method of fabricating a gas sensor comprising:
    preparing a substrate, wherein the substrate also serves as a counter electrode;
    preparing an electrolyte material;
    depositing the electrolyte on the substrate;
    preparing an organic film on the surface of the electrolyte;
    preparing a diffusion barrier, wherein the diffusion barrier also serves as a sensing electrode and comprises a dense composite membrane consisting of yttria-stabilized zirconia and a noble metal; and
    depositing the diffusion barrier on the organic film.

2. The method of claim 1, wherein the step of preparing a substrate comprises preparing a substrate by a sol-gel process.

3. The method of claim 1, wherein the step of preparing an electrolyte comprises:
    dissolving iodine in acetone;
    dispersing yttria-stabilized zirconia (YSZ) particles in the iodine and acetone solution, whereby the YSZ particles become positively charged and form a YSZ suspension; and
    applying an electric field to the YSZ suspension.

4. The method of claim 1, wherein the step of depositing an electrolyte material on the substrate comprises depositing the electrolyte on the substrate by at least one the methods of electrophoretic deposition and dry pressing.

5. The method of claim 1, further comprising drying the organic film before depositing the diffusion barrier on the organic film.

6. The method of claim 1, wherein the diffusion barrier is prepared as a colloidal solution.

7. The method of claim 1, wherein the diffusion baffler is deposited on the electrolyte by at least one of the methods of drop coating and spin coating.

8. The method of claim 1, wherein the diffusion barrier is prepared by a sol-gel process.

9. The method of claim 1, wherein the diffusion barrier includes platinum (Pt) and yttria-stabilized zirconia (YSZ), wherein the ratio of Pt to YSZ is approximately 3.5 and wherein a Pt—YSZ composite is formed with approximately 40% by volume of Pt.

10. The method of claim 1, further including drying the layers after the diffusion barrier is deposited on the electrolyte.

11. The method of claim 10, further comprising:

depositing another layer of diffusion barrier; and firing the layers to increase the density of the diffusion barrier.

12. The method of claim 1, further comprising firing the layers to form a three-layer sensor.

13. A method of fabricating a gas sensor comprising:

preparing a substrate, wherein the substrate also serves as a counter electrode;

preparing an electrolyte material; depositing the electrolyte on the substrate;

preparing an organic film on the surface of the electrolyte, wherein the step of preparing the organic film comprises:

dissolving citric acid in ethylene glycol, with an approximate molar ratio of ethylene glycol to citric acid of 3;

heating the resultant citric acid and ethylene glycol mixture to approximately 80° C. until the solution is viscous;

preparing a diffusion barrier, wherein the diffusion barrier also serves as a sensing electrode; and depositing the diffusion barrier on the organic film.

14. A method of fabricating a gas sensor comprising:

using a sol-gel process to prepare a first thin film comprising yttria-stabilized zirconia;

depositing the first yttria-stabilized zirconia film on a layer of porous lanthanum strontium manganese oxide;

depositing an organic film absent of metal ions on the surface of the first yttria-stabilized zirconia film;

depositing a second film consisting of platinum and yttria-stabilized zirconia composite on the first yttria-stabilized zirconia film coated with the organic film; and firing the first and second films together.

15. A method of preparing an oxygen sensor comprising the steps of:

preparing a diffusion barrier, wherein the diffusion barrier is a first electrode and wherein the diffusion barrier comprises platinum (Pt)-yttria-stabilized zirconia (YSZ), the Pt—YSZ composite comprising about 40% by volume Pt;

pressing the diffusion barrier into a pellet;

depositing mixed conducting oxide electrolyte powder on the diffusion barrier pellet followed by pressing;

depositing a second electrode material onto pellet followed by pressing; and sintering of the diffusion barrier, electrolyte and second electrode to form a tri-layer oxygen sensor.

16. The method of claim 15, wherein the mixed conducting oxide powder is yttria-stabilized zirconia (YSZ).

17. The method of claim 15, wherein the second electrode material is prepared by a sol-gel process.

18. The method of claim 15, wherein the second electrode material comprises platinum (Pt)-yttria-stabilized zirconia (YSZ).

19. A method of preparing an oxygen sensor comprising the steps of:

pressing an electrolyte material into a pellet with a top and bottom;

depositing a layer of electrode material on top and bottom of the electrolyte pellet by pressing, wherein the electrode/electrolyte layers have a top and bottom;

depositing a second layer of electrolyte material on both top and bottom of the electrode material, such that the layers have outer layers of electrolyte;

firing the layers of electrolyte/electrode/electrolyte/electrode/electrolyte materials to form a multilayer structure; and grinding the multilayer structure to remove the outer electrolyte layers and expose the electrode layers.

20. The method of claim 19, wherein the electrolyte material comprises yttria-stabilized zirconia (YSZ).

21. The method of claim 19, wherein the electrode material comprises platinum (Pt)-yttria-stabilized zirconia (YSZ).

* * * * *

UNITED STATES PATENT AND TRADEMARK OFFICE
CERTIFICATE OF CORRECTION

PATENT NO. : 7,018,673 B2 Page 1 of 1
APPLICATION NO. : 10/228889
DATED : March 28, 2006
INVENTOR(S) : Liu et al.

It is certified that error appears in the above-identified patent and that said Letters Patent is hereby corrected as shown below:

Col. 1, line 29, change "bum" to --burn--

Col. 11, line 46, change "$ZrOCl_2.8H_2O$ and $Y(NO_3)_3.4H_2O$" to --$ZrOCl_2·8H_2O$ and $Y(NO_3)_3·4H_2O$--

Signed and Sealed this

Seventh Day of November, 2006

JON W. DUDAS
*Director of the United States Patent and Trademark Office*

UNITED STATES PATENT AND TRADEMARK OFFICE
CERTIFICATE OF CORRECTION

PATENT NO. : 7,018,673 B2
APPLICATION NO. : 10/228889
DATED : March 28, 2006
INVENTOR(S) : Meilin Liu et al.

Page 1 of 1

It is certified that error appears in the above-identified patent and that said Letters Patent is hereby corrected as shown below:

Col. 5, line 63, change "$La_{0.9}Sr_{0.1}Ga_{0.2}Mg_{0.8}O_3$" to --$La_{0.9}Sr_{0.1}Ga_{0.2}Mg_{0.8}O_3$--

Signed and Sealed this

Eighth Day of April, 2008

JON W. DUDAS
*Director of the United States Patent and Trademark Office*